US009505806B2

(12) United States Patent
Sirko et al.

(10) Patent No.: US 9,505,806 B2
(45) Date of Patent: Nov. 29, 2016

(54) DNA VACCINE, METHOD OF INDUCING THE IMMUNE RESPONSE, METHOD OF IMMUNISATION, ANTIBODIES SPECIFICALLY RECOGNISING THE H5 HAEMAGGLUTININ OF AN INFLUENZA VIRUS AND USE OF THE DNA VACCINE

(71) Applicant: INSTYTUT BIOCHEMII I BIOFIZYKI PAN, Warsaw (PL)

(72) Inventors: Agnieszka Sirko, Warsaw (PL); Anna Góra-Sochacka, Warsaw (PL); Włodzimierz Zagórski-Ostoja, Warsaw (PL); Anna Stachyra, Warsaw (PL); Róża Sawicka, Makó Mazowiecki (PL); Bogusław Szewczyk, Gdańsk (PL); Beata Gromadzka, Gdańsk (PL); Violetta Sączyńska, Warsaw (PL); Katarzyna Florys, Iwaniska (PL); Zenon Minta, Pulawy (PL); Krzysztof Śmietanka, Puławy (PL)

(73) Assignee: INSTYTUT BIOCHEMII I BIOFIZYKI PAN, Warsaw (PL)

( * ) Notice: Subject to any disclaimer, the term of this patent is extended or adjusted under 35 U.S.C. 154(b) by 0 days.

(21) Appl. No.: 14/346,664

(22) PCT Filed: Sep. 21, 2012

(86) PCT No.: PCT/PL2012/000095

§ 371 (c)(1),
(2) Date: Mar. 21, 2014

(87) PCT Pub. No.: WO2013/043067

PCT Pub. Date: Mar. 28, 2013

(65) Prior Publication Data

US 2014/0255343 A1 Sep. 11, 2014

(30) Foreign Application Priority Data

Sep. 23, 2011 (PL) ........................................ 396415

(51) Int. Cl.
*A61K 39/145* (2006.01)
*C07K 14/005* (2006.01)

(Continued)

(52) U.S. Cl.
CPC ............ *C07K 14/005* (2013.01); *A61K 39/12* (2013.01); *A61K 39/145* (2013.01); *A61K 39/39* (2013.01);

(Continued)

(58) Field of Classification Search
None
See application file for complete search history.

(56) References Cited

U.S. PATENT DOCUMENTS

| | | | |
|---|---|---|---|
| 6,511,676 | B1 | 1/2003 | Boulikas |
| 2008/0032921 | A1 | 2/2008 | Alexander et al. |

(Continued)

FOREIGN PATENT DOCUMENTS

| | | | |
|---|---|---|---|
| EP | 1156789 | B1 | 3/2006 |
| EP | 2284260 | A1 | 2/2011 |

(Continued)

OTHER PUBLICATIONS

Suguitan, et al. The influence of the multi-basic cleavage site of the H5 hemagglutinin on the attenuation, immunogenicity and efficacy of a live attenuated influenza A H5N1 cold-adapted vaccine virus. Virology, 2009; 395(2): 280-288.*

(Continued)

*Primary Examiner* — Daniel E Kolker
*Assistant Examiner* — Stuart W Snyder
(74) *Attorney, Agent, or Firm* — Walker & Jocke

(57) ABSTRACT

The object of the invention is a DNA vaccine, method of inducing the immune response, antibodies specifically recognizing the haemagglutinin H5 of an influenza virus and application of the DNA vaccine. According to the invention, one or two-fold immunization of hens with DNA vaccine containing a cDNA encoding the modified H5 haemagglutinin HA protein, i.e. with the deletion of the cleavage site between HA subunits (this provides for greater safety of the vaccines). Moreover, the encoding region of the HA is modified in such a way that protein production in the bird cells should achieve maximal yield. The main modification is codon optimization for the hens and deletion of the site of proteolytic cleavage between subunits HA1 and HA2.

9 Claims, 4 Drawing Sheets

Figure 1:
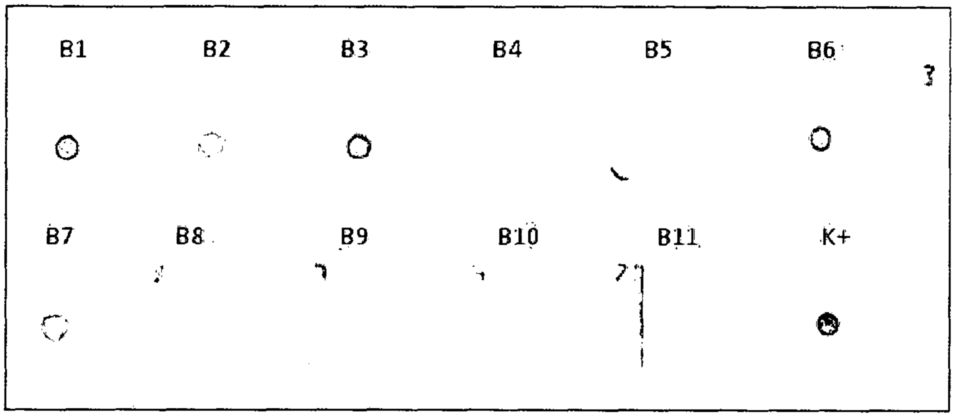

(51) Int. Cl.

| | |
|---|---|
| ***A61K 39/12*** | (2006.01) |
| ***A61K 39/39*** | (2006.01) |
| ***C07K 16/10*** | (2006.01) |
| *A61K 39/00* | (2006.01) |

(52) U.S. Cl.

CPC ....... *C07K 16/1018* (2013.01); *A61K 2039/53* (2013.01); *A61K 2039/54* (2013.01); *A61K 2039/545* (2013.01); *A61K 2039/552* (2013.01); *A61K 2039/55522* (2013.01); *A61K 2039/55533* (2013.01); *A61K 2039/55555* (2013.01); *C12N 2760/16122* (2013.01); *C12N 2760/16134* (2013.01)

(56) References Cited

U.S. PATENT DOCUMENTS

| | | | |
|---|---|---|---|
| 2009/0291472 | A1 | 11/2009 | Lu et al. |
| 2010/0160421 | A1 | 6/2010 | Fomsgaard |
| 2010/0255029 | A1 | 10/2010 | Bublot et al. |
| 2011/0065095 | A1 | 3/2011 | Kida et al. |
| 2011/0171260 | A1 | 7/2011 | Rao et al. |

FOREIGN PATENT DOCUMENTS

| | | | |
|---|---|---|---|
| WO | 2008054540 | A2 | 5/2008 |
| WO | 2008145129 | A2 | 12/2008 |
| WO | 2009092038 | A1 | 7/2009 |
| WO | 2010115133 | A2 | 10/2010 |

OTHER PUBLICATIONS

Lambert and Fauci. Influenza Vaccines for the Future. N. Engl. J. Med. 2010; 363:2036-44.*

Rumschlag-Booms et al. Comparative analysis between a low pathogenic and a high pathogenic influenza H5 hemagglutinin in cell entry. Virol. J. 2009; 6(76): 1-5 as downloaded from BioMed Central website.*

AYK02225 submitted by Butlot et al., 2010.*

Dhama, K, et al., "DNA vaccines and their applications in veterinary practice: current perspectives," Vet Res Commun, 2008, pp. 341-356, vol. 32, Springer Science, India.

Fynan, E.F., et al., "Use of DNA encoding influenza haemagglutinin as an avian influenza vaccine," DNA Cell Biol, 1993, pp. 785-789, vol. 12.

Fynan, E.F. et al., "DNA vaccines: protective immunizations by parenteral, mucosal and gene-gun inoculations," Proc Natl Acad Sci USA, 1993, pp. 11478-11482, vol. 90, USA.

Gromadzka, B. et al., "Detection of changes in avian influenza genome fragments by multitemperature single-strand conformational polymorphism," Molecular and Cellular Probes, 2008, pp. 301-304, vol. 22, Elsevier.

Kodihalli, S., et al., "Strategies for inducing protection against avian influenza A virus subtypes with DNA vaccines," Vaccine, 2000, pp. 2592-2599, vol. 18, Elsevier Science.

Kutzler, M.A., et al., "DNA vaccines: ready for prime time?," Nature Reviews: Genetics, 2008, pp. 776-788, vol. 9, Macmillan, USA.

Park, J.H, et al., "Protection of chicken against very virulent IBDV provided by in ovo priming with DNA vaccine and boosting with killed vaccine and the adjuvant effects of plasmid-encoded chicken interleukin-2 and interferon-gamma," Journal of Veterinary Science, 2009, pp. 131-139, vol. 10.

Robinson, H.L., et al., "Protection against a lethal influenza virus challenge by immunization with a haemagglutinin-expressing plasmid DNA," Vaccine, 1993, pp. 957-960, vol. 11, Butterworth-Heinemann.

Swayne, D.E., "Avian influenza vaccines and therapies for poultry," Comparative Immunology, Microbiology and Infectious Diseases, 2009, pp. 351-363, vol. 32, Elsevier B.V.

"Avian Influenza," OIE Terrestrial Manual 2012, adopted by the World Assembly of Delegates of the OIE, May 2012, pp. 436-454, Chapter 2.3.4, [http://www.oie.int/international-standard-setting/terrestrial-manual/access-online/].

Rao Srinivas et al., "Multivalent HA DNA Vaccination Protects against Highly Pathogenic H5N1 Avian Influenza Infection in Chickens and Mice", PLOS ONE, Public Library of Science, US, Jun. 1, 2008 (Jun. 1, 2008), pp. E2432-1, vol. 3, No. 6 XP002527215, ISSN: 1932-6203, DOI: 10.1371/JOURNAL.PONE.0002432.

International Search Report for App. No. PCT/PL2012/000095 filed Sep. 21, 2012.

Written Opinion of the International Searching Authority for App. No. PCT/PL2012/000095 filed Sep. 21, 2012.

Jiang et al., "Enhanced protective efficacy of H5 subtype avian influenza DNA vaccine with codon optimized HA gene in a pCAGGS plasmid vector", Antiviral Research, Elsevier BV, NL, Jun. 3, 2007 (Jun. 13, 2007), pp. 234-241, vol. 75, No. 3, 1XP022114363, ISSN: 0166-3542, DOI: 10.1016/J.ANTIVIRAL.2007.03.009.

Toro H et al., "Protection of chickens against avian influenza with nonreplicating adenovirus-vectored vaccine", Poultry Science, Champaign, IL, US, Apr. 1, 2009 (Apr. 1, 2009), pp. 867-871, vol. 88, No. 4, XP008119748, ISSN: 0032-5791, DOI: 10.3382/PS.2008-00333.

Henke Andreas et al., "Co-expression of interleukin-2 by a bicistronic plasmid increases the efficacy of DNA immunization to prevent influenza virus infections.", Intervirology 2006, 2006, pp. 249-252, vol. 49, No. 4, XP002712860, ISSN: 0300-5526.

Jeong Ho Park et al., "Protection of chicken against very virulent IBDV provided by in ovo priming with DNA vaccine and boosting with killed vaccine and the adjuvant effects of plasmid-encoded chicken interleukin-2 and interferon-[gamma]", Journal of Veterinary Science, Jan. 1, 2009 (Jan. 1, 2009), p. 131, vol. 10, No. 2, XP055079018, ISSN: 1229-845X, DOI: 10.4142/jvs.2009.10.2.131 cited in the application.

Song J M et al., "Protective immunity against H5N1 influenza virus by a single dose vaccination with virus-like particles", Virology, Elsevier, Amsterdam, NL, Sep. 15, 2010 (Sep. 15, 2010), pp. 165-175, vol. 405, No. 1, XP027180037, ISSN: 0042-6822 [retrieved on Jul. 28, 2010].

Yixin Chen et al., "Broad Cross-Protection against H5N1 Avian Influenza Virus Infection by Means of Monoclonal Antibodies that Map to Conserved Viral Epitopes", The Journal of Infectious Diseases, Jan. 1, 2009 (Jan. 1, 2009), pp. 49-58, vol. 199, No. 1, XP055023361, ISSN: 0022-1899, DOI: 10.1086/594374.

Database EMBL [Online], "Gallus gallus breed broiler interleukin-2 precursor (IL2) mRNA, complete cds.", Jul. 1, 2002 (Jul. 1, 2002), XP002712861, retrieved from EBI accession No. EM_STD:AF483599 Database accession No. AF483599.

Database EMBL [Online], "Influenza A virus (A/whooper swan/Germany/R88/06(H5N1)) HA gene for hemagglutinin, genomic RNA", Mar. 31, 2007 (Mar. 31, 2007), XP002712862, retrieved from EBI accession No. EM_STD:AM403462 Database accession No. AM403462.

* cited by examiner

DNA VACCINE, METHOD OF INDUCING THE IMMUNE RESPONSE, METHOD OF IMMUNISATION, ANTIBODIES SPECIFICALLY RECOGNISING THE H5 HAEMAGGLUTININ OF AN INFLUENZA VIRUS AND USE OF THE DNA VACCINE

The subject of the invention is a DNA vaccine, method of inducing the immune response, method of immunisation, antibodies specifically recognising the haemagglutinin of the H5 subtype of an influenza virus and use of the DNA vaccine. According to the invention, one or two-time immunisation of hens with a DNA vaccine containing the cDNA encoding the modified H5 haemagglutinin (HA) protein, i.e. with the deletion of the proteolytic cleavage site between HA subunits (this provides for greater safety of the vaccines and the expression of a "super antigen" in the form of a long, non-processed polypeptide). Moreover, the encoding region of the HA is modified in such a way that protein production in the bird cells should achieve maximal yield. The main modification is codon optimisation for the hens and deletion of the proteolysis sensitive region of HA.

Over the recent years, exceptional attention has been focused on the influenza virus, especially the highly pathogenic type of the avian influenza virus (HPAI). "Bird flu" is a serious and highly contagious disease of poultry and other breeding birds. Actually, many strains of the avian influenza virus are circulating, and some of them could also pass to mammals, in particular pigs and people. The level of threat for animal health and the public health caused by different strains of influenza viruses in the bird population is highly variable and, to a certain extent, unpredictable because of frequent point mutations and the possibility of the replacement of RNA segments between different strains. Infection with some strains of influenza viruses coming from birds might be the source of illness amongst domestic fowl. The collaborative research of epidemiologists and ornithologists led to the conclusion that it is not the migration of birds, but rather incompatibility with the obligatory sanitary-veterinary regulations of poultry breeding and trade that is responsible for the transfer of avian influenza. At present, it seems that the most effective method of counteraction for the transfer of avian influenza to people (from which an influenza pandemic could be an effect) and minimisation of potential losses in the poultry industry is immunisation of a breeding flock at risk against avian influenza viruses, especially against the highly pathogenic H5N1 strains. It is worthwhile adding that vaccination of laying hens would prevent the possible spread of the virus through the egg distribution chain and allow for the protection of chicks in their early lifespan through maternal antibodies present in the yolk of eggs.

Two main types of conventional vaccines against influenza are accepted for use on people. The first one, the most frequently used, is the classical inactivated vaccine comprising inactivated virions. In order to obtain these kinds of vaccines, the viruses must be multiplied and, after purification, subjected to chemical or physical inactivation. The second one is a live attenuated vaccine (e.g. FluMist), which consists of reassortants between a vaccine virus and a temperature sensitive virus, so-called cold adapted (And/Ann Arbor/6/60), which can multiply exclusively in temperatures up to 33° C.

At present, the conventional vaccines used are trivalent. Before every influenza season, WHO decides what strains of viruses will be the source of the recommended vaccine. Such seasonal vaccines contains three influenza viruses: one influenza virus type A subtype H3N2, one type A subtype H1N1 and one influenza type B of the virus strain. The effectiveness of inactivated vaccines is about 30%-90% depending on age and medical conditions. Live attenuated vaccines are characterised by a higher effectiveness and a broader immune response (humoral, cellular, MALT).

Actually, the availability of technology for mass production of viral particles is essential for the preparation of conventional vaccines. The most classical method used is propagation/multiplication of influenza viruses in embryonated hen eggs. After multiplication, the virus is isolated along with the amniotic fluid. This technique has some disadvantages. First of all, it is lengthy and time-consuming. Moreover, during repeated passages in chicken embryos, the glycoproteins of the vaccine virus, in particular in the HA coding gene, undergo gradual mutations which may lead to the altered antigenic profile of the vaccine. Obviously, vaccines received by this method are not suited for people allergic to egg products.

Another method of large-scale production is multiplying influenza viruses in cell cultures such as well characterised and accredited cell lines like Vera or MDCK. In comparison with breeding in embryos, the problem of the mutation of the genes of glycoproteins and contamination with allergenic chicken proteins is eliminated. However, other problems arise due to the adherent kind of cell culture, resulting in the necessity of applying micro-carrier bioreactors of a capacity reaching 10,000 liters. This means heavy costs and time-consuming production (~6 months from WHO recommendation to pharmaceutical product). Thus, an alternative to conventional vaccines is still missing.

Production of a new generation of vaccines should be fast, safe, simple, cheap and easily applicable. Such features are ascribed to subunit vaccines consisting of strong, closely defined antigens of the virus or their most immunogenic fragments. Elements of subunit vaccines might be isolated directly from pathogenic organisms, but this approach requires, once again, pathogen production on a large scale, which is dangerous and expensive. Applying the technology of the recombined DNA offers an attractive method of attaining immunogenic subunits. This technology combines the benefits of subunit vaccines with the possibility of obtaining their components in a non-pathogenic expression system, e.g. bacterial, yeast, mammalian or plant cells. This way of antigen production is fast, cheap, safe and highly efficient.

The next group of new generation vaccines are DNA vaccines (genetic vaccines), which are in fact regarded as third generation vaccines. For the first time in the early 1990s, DNA vaccines were used for immunisation of animals. Since that time, the DNA vaccine concept was tested against various pathogens. The effectiveness of DNA immunisation was shown in models of the following illnesses and pathogens: influenza type B, HBV, malaria, tuberculosis, SIV viruses and HIV type 1 and different cancers. Importantly, DNA vaccines may affect not only humoral but also cellular immunity. Moreover, two other advantages of these vaccines seem to be very important: (a) possibility of rapid design and construction of the vaccine, which allows for the avoidance of the long-term and elaborate procedure of protein expression in selected systems and their purification; and (b) attainment of an antigen of an identical structure with the version arising during infection, i.e. containing post-translational modification typical for the host, since protein production is occurring in situ, as a result of the DNA expression in immunised animal cells. It's quite easy to increase the immunogenicity of DNA vaccine rationalisation or adaptation of the encoding sequence to the antigenic sequence optimised set of codons for the given host, e.g. mouse, human.

The precise mechanism of action of genetic vaccines has been recognised rather recently. It is postulated that proteins synthesised in the host as a result of the expression of genes of pathogens engineered in the DNA vaccine "mimic" proteins produced in the course of natural pathogen infection. Briefly, the DNA plasmid is delivered to the skin or muscle by one of several delivery methods. The plasmid enters the nucleus of the transfected local cells, including resident antigen presenting cells (APCs). The expression of plasmid-encoded genes results in generation of antigenic proteins that are converted to the peptide string by the intracellular proteolytic complexes. These antigens can become the subject of immune surveillance in the context of both major histocompatibility complex (MHC) class I and class II molecules of APCs in the vaccinated organism. In draining lymph nodes, antigen-loaded APCs 'present' antigenic peptide-MHC complexes in combination with signalling costimulatory molecules to naïve T cells. This interaction results in initiation of an immune response, such as activation and expanding of T cells and activation of B cells and the antibody production process. In this way, both humoral and cellular immune responses are triggered. The details concerning current research on genetic vaccines may be found in a few review articles (Dhama et al., 2008; Kutzler and Weiner, 2008)

In May 2006, Vical Incorporated (http://www.vical.com) announced the production of a trivalent vaccine containing the DNA sequence encoding H5 antigen, nucleoprotein (NP) and M2 protein. The vaccine is administrated with the company's patented adjuvant, Vaxfectin. It was shown that 100% of immunised mice and ferrets are protected against infection from the H5N1 flu virus. The vaccine also provides a high level of protection against infection with other strains of influenza viruses.

The basic mechanisms of the immune response of birds are similar to the response of mammals. Birds also have an ability to induce the Th1 and Th2 type of immunological response and similar path of their induction. However, the type and the location of the early immune response to the DNA vaccine can be different in birds because of the presence of other lymphatic bodies. The frequently used promoter of CMV (human cytomegalovirus) is sufficiently active in bird cells in order to provide efficient expression of genes under its control. The typical administration routes of the vaccine are intramuscular injection and subcutaneous, and the first one seems to be the most effective. DNA vaccines might be injected into birds with or without any adjuvants. Some biological adjutants such as IL-2, IL-8, IL-6 and the γ interferon (IFNγ) were tested. Published data concerning the immunisation of poultry with DNA vaccines has shown positive effects in the form of the cellular, humoral or protective response. What's more, with birds in which the presence of specific antibodies wasn't demonstrated, a protective response was detected, which would suggest the appearance of a cellular rather than humoral response. Moreover, it has been recently demonstrated that immunisation of birds with the DNA vaccine encoding chicken IL-2 enhances the immunological response to the IBDV DNA vaccine (Park et al., 2009).

DNA vaccines encoding the HA protein from different strains of avian influenza viruses were also tested in poultry. In many cases, the authors didn't state the presence of anti-HA antibodies, but demonstrated effective protection against infection with lethal doses of the virus. Different ways of vaccine administration were tested, and the most effective was by using the gene gun.

Here are some examples of publications describing the use of the cDNA encoding HA to poultry immunisation: (Fynan et al., 1993; Fynan et al., 1993 b; Robinson et al., 1993; Kodihalli et al., 2000; Rao et al., 2008; Swayne, 2009).

The WO2008145129 (published 2008 Dec. 4) and US20100160421 (published 2010 Jun. 24) inventions concern vaccines and the use of the naked DNA and/or RNA molecule encoding haemagglutinin (HA) [and, optionally, encoding neuraminidase (NA) and/or matrix protein (M) and/or the nucleoprotein (NP)] from pandemic influenza as a vaccine component against present day and future (coming) H1, H2, H3, H5, H7, N1, N2, N3 containing influenza A infections in humans and/or swine. The influenza viruses mentioned in the invention included: the 1918 H1N1, the 1957 H2N2, the 1968 H3N2 influenza A virus, the high pathogenic bird pandemic ATV strain (A/buzzard/Denmark/6370/06(H5N1)), the 2001 H5N7 low pathogenic avian influenza virus (ATV) strain (A/Mallard/Denmark/64650/03 (H5N7)), the March 2006 Denmark H5N1 high pathogenic AIV strain (A/buzzard/Denmark/6370/06(H5N1)), the 2008 (A/duck/Denmark/53-147-8/08 (H7N1)), the 2004 (A/widegeon/Denmark/66174/G18/04 (H2N3)). If the vaccine components are used as DNA or RNA vaccines with or without the corresponding protein, the codons can optionally be "humanised" using preferred codons from highly expressed mammalian genes, and the administration of this DNA vaccine can be by saline or buffered saline injection of naked DNA or RNA or injection of a DNA plasmid or linear gene expressing DNA fragments coupled to particles. Addition of the matrix protein (M) and/or the nucleoprotein (NP) as protein or DNA from the 1918 influenza strain is also disclosed.

In the invention US20090291472, the codon-optimised nucleic acids encoding influenza polypeptides and uses of nucleic acids and polypeptides for inducing immune responses are described.

The invention WO2009092038 (published 2009 Jul. 23) concerns a DNA vaccine against the influenza virus and its use. Sustained outbreaks of highly pathogenic avian influenza (HPAI) H5N1 in avian species increase the risk of reassortment and adaptation to humans. The ability to stop its spread in birds would reduce this threat and help maintain the capacity for egg-based vaccine production. While vaccines offer the potential to control avian disease, a major concern of current vaccines is their inability to protect against evolving avian influenza viruses. DNA vaccines encoding haemagglutinin (HA) proteins from different HPAI H5N1 serotypes protect against the homologous and heterologous HPAI H5N1 strain challenge in animals. These vaccines elicit antibodies that neutralise multiple serotypes of HPAI H5N1 when given in combinations containing up to 10 HAs. The response is dose-dependent. The breadth of protection is determined by the choice of the influenza virus HA in the vaccine. Monovalent and trivalent HA immunogens and/or vaccines conferred complete protection in mice against a lethal H5N1 A/Vietnam/1203/2004 challenge 68 weeks after vaccination. In chickens, complete protection was conferred against heterologous strains of HPAI H5N1 after vaccination with a trivalent H5 serotype DNA vaccine with doses as low as 5 μg DNA given twice either by intramuscular needle injection or with a needle-free device.

The invention EP2023952 (published 2009 Feb. 18) provides polynucleotides and polypeptides capable of enhancing the immune response of a human in need of protection against influenza virus infection by administering in vivo, into the tissue of the human, at least one polynucleotide comprising one or more regions of nucleic acid encoding an influenza protein or a fragment, variant or derivative thereof, or at least one polypeptide encoded therefrom. The present invention also relates to identifying and preparing influenza virus epitopes and to polynucleotides and polypeptides comprising such influenza virus epitopes. The present invention also relates to compositions and methods of use in the prevention and treatment of influenza virus infection.

Despite intensive research and numerous published data, the state of the art still isn't sufficient for creating an economical vaccine for poultry that would be simple in application and, at the same time, would ensure effective protection and the possibility of distinguishing hens immunised from ones infected with a virus. Unexpectedly, it turned out that the suggested solution, according to the invention, had a chance to fill this gap.

The aims of the invention are: creating a vaccine containing the modified cDNA encoding HA protein of the H5 serotype, drawing up a method of inducing the immune response, as well as obtaining antibodies specifically recognising the H5 HA and using the DNA vaccine for obtaining antibodies recognising the H5 HA of the influenza virus. Realisation of the defined objective and solving the problems described in the state of the art with ensuring the effective protection and possibility of distinguishing between chickens immunised against and infected with the virus with simultaneous simple administration were achieved in this invention.

According to the invention, a one-dose or a two-dose immunisation of chickens with a vaccine containing DNA encoding the modified H5 HA protein with the deletion of the proteolytic cleavage site between HA subunits is proposed. This modification allows for expression of all known and prospective HA in a single continuous polypeptide not divided into separate domains. This may have a bearing on conformation of the antigen and hence exposition to the immune system, differing favourably from what has been reported in literature. Moreover, application of the modified encoding region is proposed in order to provide a high level of antigen protein production in the cells of vaccinated birds. Codons altered to the codons preferred by domestic chickens is an important modification. By applying the solution according to this invention, an immune response of the humoral type was already obtained (production of the specific antibodies) in immunised poultry after one- or two-fold immunisation. Sera taken from immunised birds provided positive results in the inhibition test (HI), which lets us assume that the antibodies could neutralise the flu virus and protect from infection.

Indeed, the challenge experiment confirmed the protective activity of the DNA vaccine that was administered two times on day 7 and 21 at a dose of 125 μg of plasmid DNA in a PBS solution with the transfection reagent Lipofectin. The immunised birds were protected against influenza virus infection, and shedding of the viruses was not observed.

Strengthening of the immune response by additional administration of the plasmid ensuring the cDNA expression of chicken interleukin 2 was observed in some cases.

The subject of the invention is a DNA vaccine containing a modified cDNA encoding the haemagglutinin H5, characterised by the presence of the deletion of the region encoding amino acids in the site of the proteolytic cleavage between HA1 and HA2 units and by optimally altered codons for hens in order to provide the maximum yield of H5 protein in bird cells after immunisation.

Preferably, when the vaccine contains the sequence determined by SEQ. ID No. 2.

Preferably, when the deletion is in a range between 15 and 21 base pairs encoding amino acids of the cleavage site between HA1 and HA2 units, preferably 18 base pairs.

The next subject of the invention is a method of induction of the humoral immune response in which specific antibodies recognising haemagglutinin H5 protein are produced, characterised by that the DNA vaccine described above is applied.

Preferably, when the immune response is enhanced by providing a plasmid ensuring the cDNA expression of chicken interleukin 2 determined by the sequence SEQ. ID No. 3.

Preferably, when the first vaccine dose is administered up to the $14^{th}$ day after hatching.

Preferably, when the manner of preparation of expression plasmids and samples for the immunisation includes lipid or macromolecular carriers.

The next subject of the invention is a method of immunisation, characterised in that, at least one dose of the DNA vaccine described above is applied.

Preferably, the first dose of the vaccine is DNA vaccine described in claims 1 to 3 and the second dose of the vaccine is the DNA vaccine or the antigenic protein, HA.

The next subject of the invention are antibodies specifically recognising the haemagglutinin 1-15 of an influenza virus, characterised by the fact that they are obtained by using the vaccine specified above.

Preferably, when antibodies are active or inactive in the test of haemagglutination inhibition using the H5 antigen of an influenza virus.

Preferably, when antibodies are able or unable to neutralise an influenza virus.

In order to better characterise the invention, it is presented in the following figures:

FIG. 1 shows the presence of anti-HA antibodies in the sera of immunised chickens. The antibodies were detected in the sera of 33-day-old chickens by dot blot. 100 ng of the HA protein (A/Bar-headed Goose/Qinghai/12/05; Immune Technology) was used as a control antigen that was spotted on the membrane directly. Each piece of the membrane containing the control antigen was incubated with the sera of chickens of the designated group (B1-B11). The chicken antibodies were next detected with appropriate secondary antibodies. K(+)-positive control (HI AIV H5-positive) from the National Veterinary Research Institute in Pulawy. The numbers of groups (B1-B11) are given above the corresponding results of the test; descriptions of the groups are in scheme A.

Figure 2:
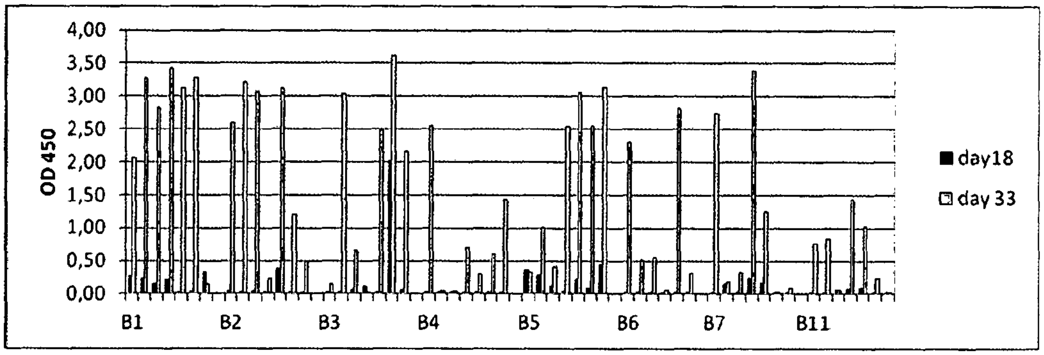

FIG. 2 shows the presence of anti-HA antibodies detected by ELISA assay in the sera of individual chickens from the indicated groups on two indicated dates (day 18 and day 33). The numbers of the groups are explained in scheme A. K(+)-positive serum from chickens immunised with a sample containing the membrane fraction of recombined baculovirus AcMNPV carrying the full length HA gene.

Figure 3:
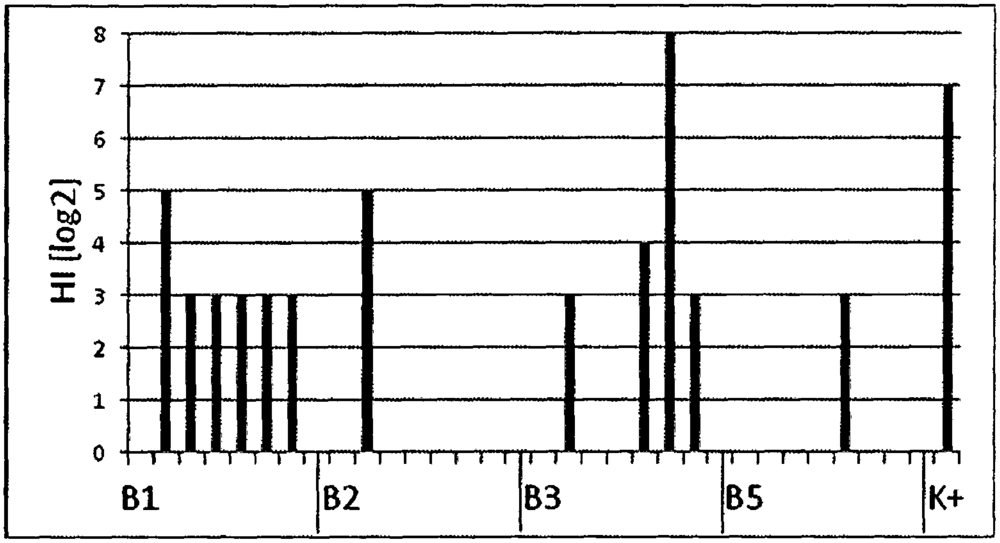

FIG. 3 shows the results of the HI test of selected chickens immunised according to scheme A. K(+)-positive control (HI anti-serum for AI H5N2; GD Deventer, Netherlands).

Figure 4:
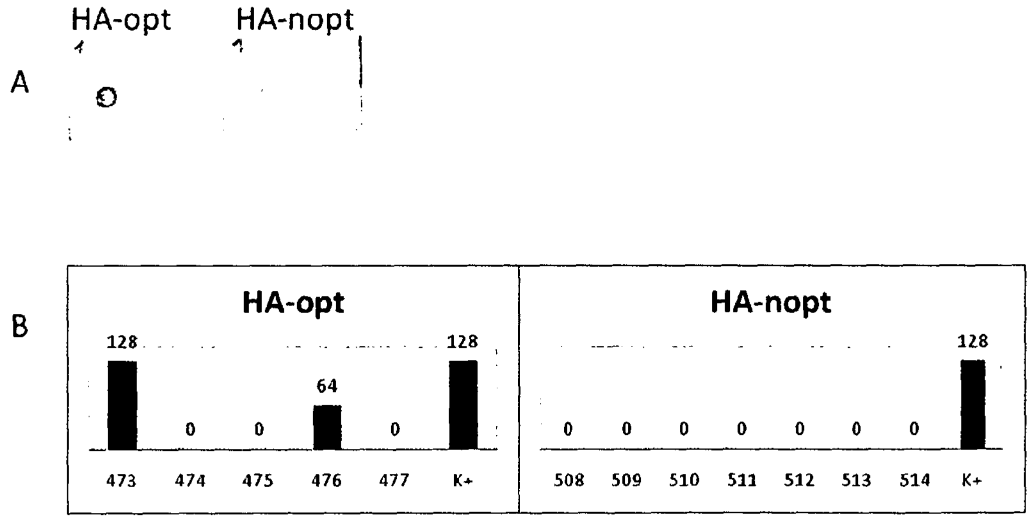

FIG. 4 shows the comparison between the response to immunisation with DNA with optimised codons (HA-opt) and with non-optimised codons (HA-nopt). A—results of the dot blot showing anti-HA antibodies in the sera pooled from all chickens of examined groups. B—results of the HI test of individual chickens (indicated by numbers) from both groups; K(+) positive control; the numbers under the bars indicate the highest serum dilutions providing a positive response.

Figure 5:
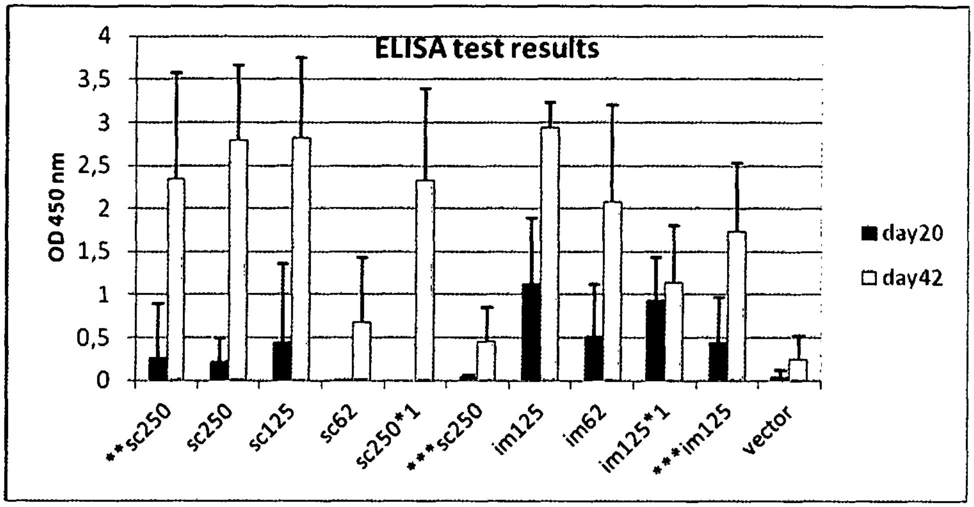
Figure 6:
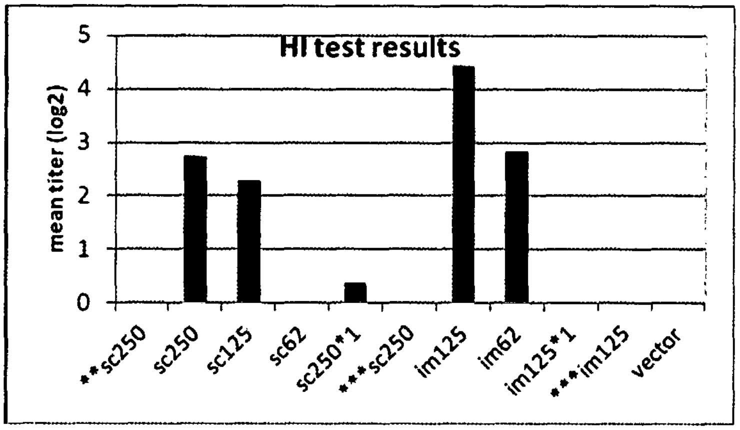
Figure 7:
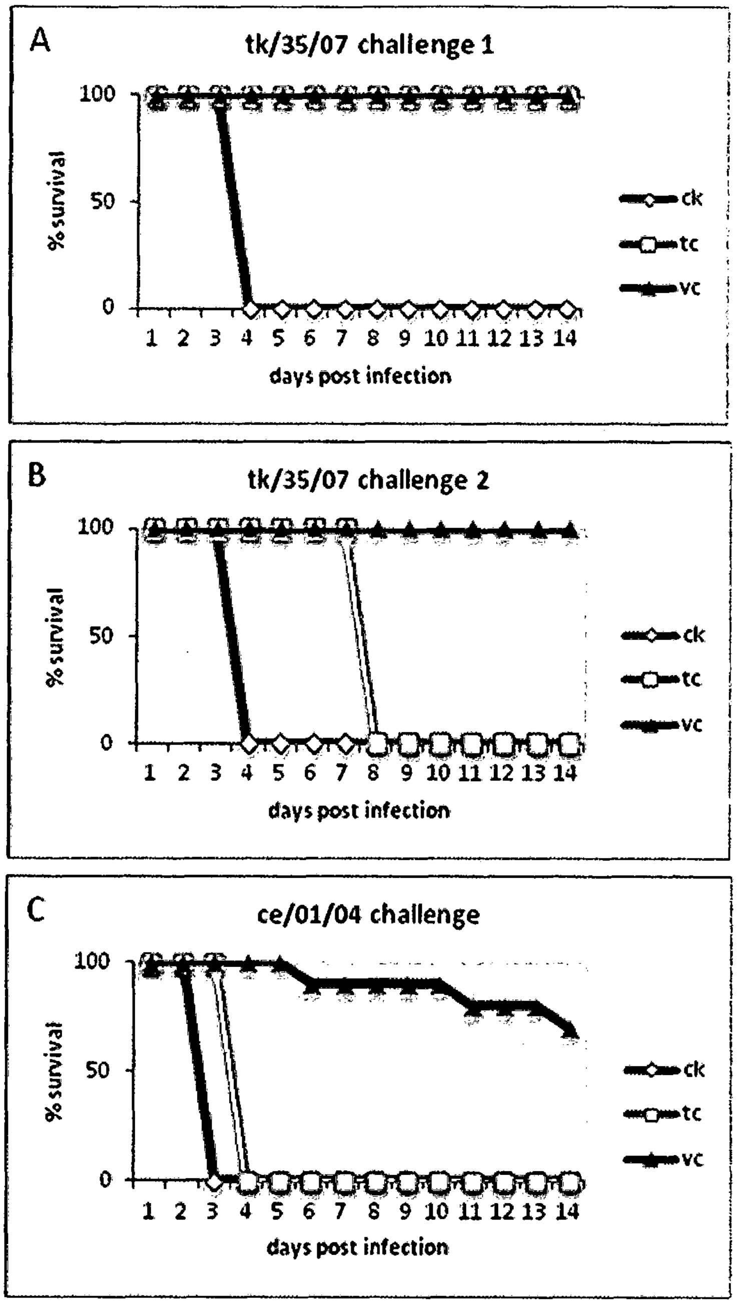

FIG. 5 shows the results of the ELISA test detecting anti-HA IgY in the sera of vaccinated chickens. Samples were collected two weeks after the first immunisation (day 20) and three weeks after the second immunisation (day 42). The data is shown as mean titers with the SD of each group (optical density at 450 nm). *group received one dose, wild type HA sequence, *immunisation without a liposomal carrier FIG. 6 shows the results of the Haemagglutination Inhibition test detecting anti-HA antibodies in the serum of vaccinated chickens. Samples were collected three weeks after the second immunisation (day 42). Sera without detectable HI were assigned a titer of 0. The data is shown as mean titers with the SD of each group ($log_2$ from the reciprocal of the highest dilution providing positive result). *group received one dose, non-optimised HA sequence, *immunisation without a liposomal carrier FIG. 7 shows the results of the avian influenza virus (AIV) challenge experiment with a homologus strain 3 weeks (A) and 8 weeks (B) after final vaccination, and with a heterologous strain (from a different clad) 3 weeks after the final vaccination (C). The data is shown as % of the survival ratio in the respective groups (ck—control chickens, tc—transmission chickens, vc—vaccinated chickens).

In order to better understand the invention, examples are listed below.

EXAMPLES

Example I

Preparation of the Expression Plasmids and Vaccine Dosages for Immunisation

The cDNA carrying the open coding frame of the full-length haemagglutinin were obtained in the reverse transcription and amplification reaction (RT-PCR) using as a template the RNA of the Polish strain of influenza virus H5N1 (A/swan/Poland/305-135V08/2006); EpiFluDatabase Acc. No. EP1156789; http://platform.gisaid.org; (Gromadzka et al., 2008). The nucleotide sequence is presented as SEQ. ID No. 1. Next, cDNA with deletion of the 18 nucleotides encoding amino acids 341-346 (RRRKKR at the site of proteolytic cleavage between subunits HA1 and HA2) was synthesised. Additionally, the sequence was optimised for the domestic chicken (*Gallus gallus*) codon bias. The sequence is 100% identical at the amino acid level and 76% at nucleotide level compared with the wild type sequence of haemagglutinin (including the 18 nucleotide deletion described above) of the Polish H5N1 strain. A cDNA of 1689 bp length coding HA protein corresponding to 1-568 amino acids of HA (with the deletion between the 341-346 aa position) was cloned into the pCI (Promega) vector (restriction sites MluI and SalI) resulting in a K3 plasmid construct. The sequencing of the recombinant plasmid confirmed the correct sequence of the cloned cDNA coding HA, and the sequence is presented as SEQ. ID No. 2. In a similar way, the pIL2 plasmid carrying cDNA of chicken interleukin 2 (chIL-2) was prepared. The IL-2 cDNA was retrieved from the U.D. chick EST database [http://www.chickest.udel.edu] clone number pat.pk0036.g8 (GenBank AF017645). The sequence of chIL-2 is presented as SEQ. ID No. 3.

The obtained recombinant plasmids were transformed into bacterial cells, *Escherichia coli* DH5α. The recombinant plasmid DNA was isolated and purified using a NoEndo Jetstar 2.0 Plasmid Giga Kit (Genomed). The concentration and purity of the DNAs were estimated spectrophotometrically at $OD_{260}$ and by separation in agarose gels. Vaccine doses were prepared by mixing DNA with a Lipofectin transfection reagent (Invitrogen) solution prepared according to the manufacture's procedure. The plasmids were mixed with the prepared solution of Lipofectin in a 6:1 ratio (μg DNA:μl Lipofectin) or 12:1 for a mixture of one plasmid or two kinds of plasmids, respectively.

Example II

Subcutaneous Immunisation of Chickens and Collection of Samples for Analysis Chickens were immunised according to scheme A.

Scheme A of the experiment of subcutaneous immunisation of broiler chickens

| Group No. | Formulation | Priming immunisation (on day 3) Dose | Boosting immunisation (on day 17) Dose | No. of chickens |
|---|---|---|---|---|
| B1 | K3 | 250 μg | 250 μg | 7 |
| B2 | K3 | 125 μg | 125 μg | 7 |
| B3 | K3 + IL2 | 125 μg + 125 μg | 125 μg + 125 μg | 7 |
| B4 | K3 | 62.5 μg | 62.5 μg | 7 |
| B5 | K3 + IL2 | 62.5 μg + 125 μg | 62 μg + 125 μg | 7 |
| B6 | K3 | 31.25 μg | 31.25 μg | 7 |
| B7 | K3 + IL2 | 31.25 μg + 125 μg | 31.25 μg + 125 μg | 7 |
| B8 | pCi | 250 μg | 250 μg | 7 |
| B9 | IL2 | 125 μg | 125 μg | 7 |
| B10 | lipofectin | — | — | 7 |
| B11 | K3 (-lipofectin) | 250 μg | 250 μg | 7 |

Immunisation According Scheme A.

Vaccines were administered subcutaneous in the neck on day 3 and 17 of life. Different doses of DNA vaccines were administered: 250, 125, 62.5 and 31 μg; all in 400 μl volume. In addition, each dose was tested in two variants, one with plasmid encoding interleukin 2 and the second one without this plasmid. As negative controls, the groups were injected with an empty vector (250 ug) or chIL-2 plasmid (125 μg) or K3 plasmid without Lipofectin or with Lipofectin alone (without DNA). Blood samples were taken from the wing vein on day 16 and 33 of life. The blood was coagulated at room temperature over 2 h then moved to 4° C. Blood clots were centrifuged at 5,000×g at 4° C. for 10 minutes. The sera prepared in such a way were kept at −20° C.

Example III

Analysis of Immunological Response by Dot Blot

The presence of specific anti-HA antibodies in sera collected from immunised chickens were detected by dot blots. Samples of 100 ng of HA protein (A/Bar-headed Goose/Quinghai/12/05; Immune Technology) were spotted onto a nitrocellulose membrane. Equal volumes of sera derived from individual chickens of the same group were pooled and diluted 1:200 and incubated for 1 hour with a nitrocellulose membrane carrying the spotted antigen (HA protein). Secondary antibodies, anti-chicken IgY-AP, were used, and for their detection, an alkaline phosphate substrate (Roche) was applied. The results indicated the presence of the specific anti-HA antibodies in chickens immunised with K3 and K3+chIL-2. The chIL-2 seemed to enhance the humoral response, but only in the case of a low dose DNA vaccine (Groups B4-B7) that was 31.2-62.5 μg of K3 plasmid.

Example IV

Analysis of Immunological Response by ELISA Assay

The ELISA assay was used to evaluate the presence of anti-HA antibodies. The plates (MaxiSorp, Nunc) were coated with a control recombinant antigen (A/Bar-headed Goose/Quinghai/12/05; Immune Technology) at a concentration of 3 μg/ml in a PBS buffer. The plates without coating by antigens were used to estimate the nonspecific background. The coating was performed over night at 4° C. The sera were diluted 1:100 or 1:50 in PBSS (PBS+NaCl) and, for detection, mouse anti-chicken IgY (γ-chain specific) as the secondary antibodies. The goat anti-mouse IgG-HRP was then used. As a substrate for horseradish peroxidase HRP, a TMB chromogen substrate solution (Sigma) was used. After 30 min. incubation with TMB at room temperature, the reaction was stopped by 0.5 M $H_2SO_4$. The sample was denoted as positive when its absorbance value measured at $OD_{450}$ was two times higher than the arithmetic mean of the control groups.

As shown in FIG. 2, in the groups immunised with the K3 plasmid, a strong immunological response was detected. The response was directly proportional to the dose of administered plasmid DNA. The results were in agreement with the ones obtained in dot blots (FIG. 1). Moreover, positive signals were also observed in the samples collected earlier, namely 14 days after the first immunisation, e.g. on day 18 of the chicken's life. However, the titer was rather low, and the specific antibodies were only detected in some of the immunised chickens. 100% of the chickens of groups immunised with the highest dose of K3 plasmid DNA showed a high level of specific antibodies in the sera from the second term of blood collection (day 33).

Analysis of the results of the immunisation experiment showed a direct relationship of the immunological response to the DNA dose. The results also suggest that the plasmid containing the chIL-2 expression cassette stimulates the immunological response (the anti-HA antibodies level) only when low doses of K3 plasmid were applied. This is in agreement with the dot blot results.

Example V

Analysis of the Immunological Response by the Haemagglutination Inhibition (HI) Test In order to detect antibodies able to inhibit the haemagglutination process, an HI test was performed. The HI test is based on the affinity of antibodies in the sera of immunised chickens to the H5 antigen of low pathogenicity strain H5N2. The homology of the amino acid sequence of the strain used and the vaccine antigen was 91% (data not shown). The HI test was conducted according to the standard procedure (Avian Influenza in: OIE Manual of Diagnostic Tests and Vaccines for Terrestrial Animals, 2010). Samples (25 μl) of the serial two-fold dilutions (1:8 to 1:512) of the sera were incubated with 4 units of HA of the heterologous inactivated H5N2 antigen (GD Deventer, Netherlands) in titration plates at room temperature. After 25 min. of incubation, 25 μl of 1% hen erythrocytes was added and incubated for 30 min. The reciprocal of the highest dilution which inhibits agglutination of the hen's erythrocytes denotes the value of the HI of the examined sera. Samples were assigned as positive at a titer value ≥8.

The titers of particular hens were shown as $log_2$.

No antibodies inhibiting haemagglutination were detected in any group of chickens after the first collection of blood (day 18). In the sera collected on day 33, neutralising antibodies were detected in the groups vaccinated with the K3 plasmid. The best results were observed among chickens immunised with the highest dose of K3 (FIG. 3; B1 group).

Example VI

Comparison of the Immunological Response on the DNA Vaccine Containing Optimised and Non-Optimised cDNA Two groups of chickens were immunised twice on day 6 and on day 21 of life. The vaccines were administered subcutaneous. The first group was immunised with 250 μg of K3 plasmid carrying modified cDNA (SEQ. 2). The second one was immunised with 250 μg of the non-optimised coding sequence (SEQ. 1). Sera collected on day 42 were used to evaluate the specific anti-HA antibodies. The immunological response was evaluated by the technique of the dot blot and HI tests described in Example III. The results showed that the vaccine containing modified cDNA was more efficient than the non-modified one (FIG. 4).

Example VII

Comparison of Two Routes of Vaccine Administration: Subcutaneous and Intramuscular Chickens were immunised according to scheme B. 7-day old broiler chickens were divided into 11 groups, immunised twice 2 weeks apart, as indicated in scheme B, and slaughtered 3 weeks following the second immunisation. The birds were immunised intramuscularly in the breast muscle or subcutaneously in the neck with 250, 125 or 62 μg of DNA in a final volume of 320, 160 or 100 μl, respectively. Two groups received only one dose of the experimental vaccine, and two groups received plain DNA without the liposomal carrier (scheme B). Blood samples were collected twice, on day 20—before boost immunisation, and on day 42—3 weeks after the second (boosting) immunisation. Sera were prepared as described in Example II. The evaluation of the immunological response to the DNA vaccination was conducted by ELISA assay and the HI test exactly as described in Example IV and V. On day 20, when blood samples were collected for the first time (two weeks after the priming immunisation), the response was still undeveloped, and antibody titers were low (FIG. 5). After the boosting immunisation, the titers increased sharply, and some of the tested groups presented strong positive results, including the groups immunised with 250 μg and 125 μg administered subcutaneously or with 125 μg of plasmid DNA administered intramuscularly. The worst results were obtained in the group without the liposomal carrier injected subcutaneously and in a group where individuals received 60 μg of DNA also injected subcutaneously. A summary of these results is listed in Table 1.

TABLE 1

Results of immunisation experiments

| Group No. | Immunisation | Results (day 20) ELISA | Results (day 42) ELISA | Results (day 42) HI | % positive per group (day 42) ELISA | % positive per group (day 42) HI |
|---|---|---|---|---|---|---|
| 1 | **sc250 | 1/7 | 4/7 | 0/7 | 57% | 0% |
| 2 | sc250 | 1/12 | 11/12 | 5/12 | 92% | 42% |
| 3 | sc125 | 3/15 | 13/15 | 8/15 | 87% | 53% |
| 4 | sc62 | 0/7 | 3/7 | 0/7 | 43% | 0% |
| 5 | *sc250 | 0/8 | 5/8 | 1/8 | 63% | 12% |
| 6 | ***sc250 | 0/7 | 3/7 | 0/7 | 43% | 0% |
| 7 | im125 | 9/12 | 12/12 | 10/12 | 100% | 83% |
| 8 | im62 | 5/12 | 10/12 | 7/12 | 83% | 58% |
| 9 | *im125 | 9/12 | 10/12 | | 83% | |
| 10 | ***im125 | 3/12 | 12/12 | | 100% | |
| 11 | pCI vector | 0/10 | 0/10 | 0/10 | 0% | 0% |

sc—subcutaneous,
im—intramuscular,
*group received one dose,
**wild type HA sequence,
***immunisation without liposomal carrier Scheme B of subcutaneous and intramuscular chicken immunisation.

| Group No. | Priming immunisation Formulation | Priming immunisation Dosage (μg) | Boosting immunisation (2 weeks after priming) Formulation | Boosting immunisation (2 weeks after priming) Dosage (μg) | No. of chickens in a group |
|---|---|---|---|---|---|
| 1 | HA sc | 250 | HA opt sc | 250 | 7 |
| 2 | HA opt sc | 250 | HA opt sc | 250 | 12 |
| 3 | HA opt sc | 125 | HA opt sc | 125 | 15 |
| 4 | HA opt sc | 62 | HA opt sc | 62 | 7 |
| 5 | — | — | HA opt sc | 250 | 8 |
| 6 | HA opt sc-L | 250 | HA opt sc-L | 250 | 7 |
| 7 | HA opt im | 125 | HA opt im | 125 | 12 |
| 8 | HA opt im | 62 | HA opt im | 62 | 12 |
| 9 | HA opt im | 125 | — | — | 12 |
| 10 | HA opt im-L | 125 | HA opt im-L | 125 | 12 |
| 11 | pCI vector | 125 | pCI vector | 125 | 10 |

HA—haemagglutinine construct,
HAopt—haemagglutinin optimised construct,
sc—subcutaneous,
im—intramuscular,
-L—without a liposomal carrier The results obtained in the haemagglutination inhibition test were less obvious. Nevertheless, anti-HA antibodies at a level associated with protection against the influenza virus were detected (FIG. 6). After the priming immunisation, there were no detectable responses (data not shown), although 3 weeks after boosting, the immune response rose. The highest titers of antibodies were detected in the group vaccinated intramuscularly with 125 μg of DNA, where the mean titer ($log_2$) was greater than 4, which is usually taken as a protective level. No positive results were found in groups immunised with wild type (non-optimised codones) HA, immunised without liposomal carrier and immunised subcutaneously with 60 μg of the plasmid DNA.

Based on those two assays (ELISA and HI), the intramuscular route of two doses of experimental vaccine was considered to be the most promising scheme and was chosen for the challenge experiment.

Example VIII

Challenge Experiment

The HPAI/H5N1/turkey/35/07 and A/crested eagle/Belgium/01/04 influenza virus strains were cultivated in the allantoic cavities of embryonated chicken eggs in the National Veterinary Research Institute in biosafety level 3 conditions. SPF chickens were immunised intramuscularly twice with 125 μg of plasmid DNA as previously described (Example VI). The control chickens remained untreated. 3 or 8 weeks after the second immunisation, the animals were inoculated intranasally (conjunctively) with $10^6EID_{50}$ of the virus. 24 hours after inoculation, one or two untreated chickens were added to the group of vaccinated and infected chickens to monitor virus transmission. Scheme C shows the details of this experiment. The birds were monitored daily for 14 days for signs of disease. Tracheal and cloacal swabs were collected on day 3, 7 and 10 p.i. in order to monitor virus proliferation. The animals were slaughtered 2 weeks after the challenge. Samples of several organs were taken from the birds that died during the observation.

Scheme C of challenge experiment of SPF chickens

| Group No. | Priming immunisation day | Boosting immunisation day | Virus infection day | Virus infection virus | No. of chickens in a group |
|---|---|---|---|---|---|
| 1 | 7 | 21 | 42 | A/tk/35/07 | 10 (+2) |
| 2 | 7 | 21 | 77 | A/tk/35/07 | 5 (+1) |
| 3 | — | — | 42 | A/tk/35/07 | 5 |
| 4 | 7 | 21 | 42 | A/ce/01/04 | 10 (+2) |
| 5 | — | — | 42 | A/ce/01/04 | 5 |

All groups of control chickens showed replication of the influenza virus at high titers. Moreover, these chickens showed signs of disease of pathogenic AI and died 2 or 3 days after infection. The immunised group challenged with the homologues strain had no signs of infection and most had no virus replication. All birds in this group survived. In the group challenged 3 weeks after the second vaccination, two transmission control chickens also survived the challenge clinically healthy. The immunised chickens were completely protected from the lethal challenge without any clinical signs and virus shedding. In the group challenged 8 weeks after the second vaccination, one of two control chickens had detectable virus replication and died on day 7 after infection (FIGS. 7A and 7B).

In the group challenged with the heterologous strain, the majority of chickens had no signs of infection and no virus replication; however, 3 birds died at 5, 10 and 13 days after infection. The last one had no detectable virus replication in swabs and organs. The survival ratio was 70%. Two transmission control chickens had detectable virus replication and died on day 3 and 4 p.i. (FIG. 7C).

REFERENCES

Avian Influenza in: OIE Manual of Diagnostic Tests and Vaccines for Terrestrial Animals 2010 [http://www.oie.int/international-standard-setting/terrestrial-manual/access-online/]

Dhama, K., Mahendran, M., Gupta, P. K. and Rai, A. (2008). DNA vaccines and their applications in veterinary practice: current perspectives. *Vet Res Commun* 32, 341-356.

Fynan, E. F., Robinson, H. L., and Webster, R. G. (1993a). Use of DNA encoding influenza haemagglutinin as an avian influenza vaccine. DNA Cell Biol 12, 785-789.

Fynan, E. F., Webster, R. G., Fuller, D. H., Haynes, J. R., Santoro, J. C. and Robinson, H. L. (1993b). DNA vaccines: protective immunizations by parenteral, mucosal and gene-gun inoculations. Proc Natl Acad Sci USA 90, 11478-11482.

Gromadzka, B., Smietanka, K., Dragun, J., Minta, Z., Gora-Sochacka, A. and Szewczyk, B. (2008). Detection of changes in avian influenza genome fragments by multi-temperature single-strand conformational polymorphism. Mol Cell Probes 22, 301-304.

Kodihalli, S., Kobasa, D. L. and Webster, R. G. (2000). Strategies for inducing protection against avian influenza A virus subtypes with DNA vaccines. Vaccine 18, 2592-2599.

Kutzler, M. A. and Weiner, D. B. (2008) DNA vaccines: ready for prime time? *Nat Rev Genet* 9, 776-788.

Park, J. H., Sung, H. W., Yoon, B. I. and Kwon, H. M. (2009). Protection of chicken against very virulent IBDV provided by in ovo priming with DNA vaccine and boosting with killed vaccine and the adjuvant effects of plasmid-encoded chicken interleukin-2 and interferon-gamma. J Vet Sci 10, 131-139.

Rao, S., Kong, W. P., Wei, C. J., Yang, Z. Y., Nason, M., Styles, D., DeTolla, L. J., Panda, A., Sorrell, E. M., Song, H., Wan, H., Ramirez-Nieto, G. C., Perez, D. and Nabel, G. J. (2008). Multivalent HA DNA vaccination protects against highly pathogenic H5N1 avian influenza infection in chickens and mice. PLoS One 3, e2432.

Robinson, H. L., Hunt, L. A., and Webster, R. G. (1993). Protection against a lethal influenza virus challenge by immunization with a haemagglutinin-expressing plasmid DNA. Vaccine 11, 957-960.

Swayne, D. E. (2009). Avian influenza vaccines and therapies for poultry. Comp Immunol Microbiol Infect Dis 32, 351-363.

The invention claimed is:

1. A vaccine comprising, a polynucleotide comprising a modified nucleotide sequence encoding a H5 haemagglutinin of an influenza virus, wherein the nucleotide sequence contains a deletion of a region encoding the amino acids at the proteolytic cleavage site between subunits HA1 and HA2, wherein the nucleotide sequence comprises codons altered for optimization for maximal expression of the H5 haemagglutinin in bird cells, and wherein the nucleotide sequence comprises the sequence defined as SEQ. ID No. 2.

2. The vaccine of claim 1, wherein the nucleotide sequence contains a deletion of 18 base pairs encoding the amino acids at the site of proteolytic cleavage site between subunits HA1 and HA2.

3. A method comprising:

administering the vaccine of claim 1 to poultry.

4. The method of claim 3 further comprising obtaining antibodies from the immunized poultry;

wherein the antibodies specifically recognize the H5 haemagglutinin of the influenza virus encoded by the polynucleotide of claim 1.

5. The method of claim 3, further comprising administration of a polynucleotide comprising the nucleotide sequence of chicken interleukin 2 according to SEQ. ID No. 3.

6. The method of claim 3, further comprising administering the vaccine to the poultry up to 14 days after the poultry hatch.

7. The method of claim 3, further comprising:

preparing a DNA suspension in a lipid or macromolecular carrier, wherein the DNA of the suspension comprises the polynucleotide according to claim 1.

8. A method comprising:

administering the vaccine of claim 1 to poultry, and repeating the administering of the vaccine at least once to the poultry.

9. A method comprising:

administering the vaccine of claim 1 to poultry, and subsequently administering the vaccine of claim 2 or the H5 hemagglutinin protein encoded by the polynucleotide according to claim 2 to the poultry.

* * * * *

SEQUENCE LISTING

```
<160> NUMBER OF SEQ ID NOS: 3

<210> SEQ ID NO 1
<211> LENGTH: 1707
<212> TYPE: DNA
<213> ORGANISM: Influenza virus

<400> SEQUENCE: 1

atggagaaaa tagtgcttct ttttgcaata gtcagtcttg ttaaaagtga tcagatttgc     60

attggttacc atgcaaacaa ctcgacagag caggttgaca caataatgga aaagaacgtc    120

actgttacac acgcccaaga catactggaa aagacacaca acgggaagct ctgcgatcta    180

gatggagtga agcctctaat tttaagagat tgtagtgtag ctggatggct cctcgggaac    240

ccaatgtgtg acgaattcct caatgtgccg gaatggtctt acatagtgga gaagatcaat    300

ccagccaatg acctctgtta cccagggaat ttcaacgact atgaagaact gaaacaccta    360

ttgagcagaa taaaccattt tgagaaaatt cagatcatcc ccaaaagttc ttggtcagat    420

catgaagcct catcaggggt gagctcagca tgtccatacc agggaaggtc ctcctttttt    480

agaaatgtgg tatggcttat caaaaaggac aatgcatacc caacaataaa gagaagctac    540

aataatacca accaagaaga tcttttggta ctgtggggga ttcaccatcc aaatgatgcg    600

gcagagcaga caaggctcta tcaaaaccca accacctata tttccgttgg gacatcaaca    660

ctaaaccaga gattggtacc aaaaatagct actagatcca aggtaaacgg gcaaagtgga    720

aggatggagt tcttttggac aattttaaaa ccgaatgatg caataaactt tgagagtaat    780

ggaaatttca ttgctccaga aaatgcatac aaaattgtca agaaagggga ctcaacaatt    840

atgaaaagtg aattggaata tggtaactgc aacaccaagt gtcaaactcc aataggggcg    900

ataaactcta gtatgccatt ccacaacatc caccctctca ccatcgggga atgccccaaa    960

tatgtgaaat caaacagatt agtccttgcg actgggctca gaaatagccc tcaaggagag   1020
```

agaagaagaa aaaagagagg actatttgga gctatagcag gttttataga gggaggatgg 1080
cagggaatgg tagatggttg gtatgggtac caccatagca acgagcaggg gagtgggtac 1140
gctgcagaca aagaatccac tcaaaaggca atagatggag tcaccaataa ggtcaactcg 1200
atcattaaca aaatgaacac tcagtttgag gccgttggaa gggaatttaa taacttagaa 1260
aggagaatag aaaatttaaa caagaagatg gaagacggat tcctagatgt ctggacttat 1320
aatgctgaac ttctggttct catggaaaat gagagaactc tagactttca tgactcaaat 1380
gtcaagaacc tttacgacaa ggtccgacta cagcttaggg ataatgcaaa ggagcttggt 1440
aacggttgtt tcgagttcta tcacagatgt gataatgaat gcatggaaag tgtaagaaac 1500
ggaacgtatg actacccgca gtattcagaa gaagcaagat taaaaagaga ggaaataagt 1560
ggagtaaaat tggaatcaat aggaacctac caaatactgt caatttattc aacagtggcg 1620
agctccctag cactggcaat catggtggct ggtctatctt tatggatgtg ctccaatgga 1680
tcgttacaat gcagaatttg catttaa 1707

<210> SEQ ID NO 2
<211> LENGTH: 1689
<212> TYPE: DNA
<213> ORGANISM: Artificial Sequence
<220> FEATURE:
<223> OTHER INFORMATION: Nucleotide sequence of HA gene (_RRRKKR) optimised to Gallus gallus

<400> SEQUENCE: 2
atggaaaaga ttgtgctgct gtttgctatc gtgtccctgg tgaaaagcga ccagatttgt 60
atcgggtatc atgccaataa ctcaaccgaa caggtggata ctattatgga gaaaaacgtg 120
actgtgaccc acgcccagga catcctggag aagacccata acggcaaact gtgcgatctg 180
gacggagtga agcccctgat cctgcgcgat tgcagcgtgg ctggctggct gctgggaaac 240
cctatgtgcg acgagttcct gaatgtgcca gaatggtcct acatcgtgga gaaaattaac 300
ccagcaaatg atctgtgcta ccccggcaac ttcaatgact atgaggaact gaagcacctg 360
ctgtctagga tcaaccattt cgaaaagatc cagatcatcc ctaagagctc ctggagcgat 420
cacgaggctt cttcaggcgt gagtagcgca tgtccatacc agggacgctc ctctttcttt 480
cggaacgtgg tgtggctgat taagaaagac aatgcttacc caactatcaa acgcagctat 540
aacaatacca accaggaaga tctgctggtg ctgtggggaa tccaccatcc caacgacgcc 600
gctgagcaga cacggctgta ccagaatcct accacatata ttagtgtggg gacaagcact 660
ctgaaccaga gactggtgcc caagatcgca acaaggagca aagtgaatgg ccagtccgga 720
agaatggagt tcttttggac tatcctgaag ccaaacgatg ccattaattt cgaatctaac 780
ggcaacttca tcgcacccga gaacgcctac aagattgtga agaaaggaga ctccactatc 840
atgaaatctg agctggaata tgggaactgc aataccaagt gtcagacacc tatcggtgca 900
attaactcaa gtatgccctt tcacaatatc catcctctga ccattgggga gtgccccaag 960
tacgtgaaaa gtaaccgcct ggtgctggcc acaggtctgc ggaatagccc tcagggggaa 1020
ggtctgttcg gggctatcgc aggttttatt gagggcggat ggcagggaat ggtggatggg 1080
tggtacggtt atcaccattc aaacgaacag ggcagtggat acgcagccga taaggagtca 1140
acacagaaag ccattgacgg agtgactaac aaggtgaact ccatcattaa caaaatgaac 1200
acccagttcg aggctgtggg gagagagttc aacaatctgg agagaaggat cgaaaacctg 1260
aataagaaaa tggaagatgg cttcctggac gtgtggactt acaacgctga gctgctggtg 1320

-continued

```
ctgatggaga atgaaaggac cctggatttt cacgacagca acgtgaagaa tctgtatgat   1380

aaagtgagac tgcagctgag ggacaacgca aaggaactgg ggaatggttg tttcgagttt   1440

taccatagat gcgataacga gtgtatggaa tccgtgagga atggcacata cgactatcca   1500

cagtattctg aggaagcccg cctgaagcgg gaggaaattt ctggggtgaa actggagtca   1560

atcggtacct accagatcct gtctatctac tcaacagtgg ctagctccct ggccctggct   1620

atcatggtgg ctggcctgag cctgtggatg tgctctaacg gtagcctgca gtgtaggatc   1680

tgtatttga                                                           1689


<210> SEQ ID NO 3
<211> LENGTH: 432
<212> TYPE: DNA
<213> ORGANISM: Gallus gallus

<400> SEQUENCE: 3

atgatgtgca aagtactgat ctttggctgt atttcggtag caatgctaat gactacagct     60

tatggagcat ctctatcatc agcaaaaagg aaacctcttc aaacattaat aaaggattta    120

gaaatattgg aaaatatcaa gaacaagatt catctcgagc tctacacacc aactgagacc    180

caggagtgca cccagcaaac tctgcagtgt tacctgggag aagtggttac tctgaagaaa    240

gaaactgaag atgacactga aattaaagaa gaatttgtaa ctgctattca aaatatcgaa    300

aagaacctca agagtcttac gggtctaaat cacaccggaa gtgaatgcaa gatctgtgaa    360

gctaacaaca agaaaaaatt tcctgatttt ctccatgaac tgaccaactt tgtgagatat    420

ctgcaaaaat aa                                                        432
```